(«12») United States Patent
Nam et al.

(10) Patent No.: US 9,655,578 B2
(45) Date of Patent: May 23, 2017

(54) MAMMOGRAPHY APPARATUS

(71) Applicant: Samsung Electronics Co., Ltd., Suwon-si (KR)

(72) Inventors: Han Ju Nam, Anyang-si (KR); Jin-Ho Choi, Anyang-si (KR)

(73) Assignee: SANSUNG ELECTRONICS CO., LTD., Suwon-si (KR)

( * ) Notice: Subject to any disclaimer, the term of this patent is extended or adjusted under 35 U.S.C. 154(b) by 78 days.

(21) Appl. No.: 14/844,106

(22) Filed: Sep. 3, 2015

(65) Prior Publication Data

US 2016/0135772 A1    May 19, 2016

(30) Foreign Application Priority Data

Nov. 14, 2014   (KR) .................... 10-2014-0158562

(51) Int. Cl.
*A61B 6/00*   (2006.01)
*A61B 6/04*   (2006.01)

(52) U.S. Cl.
CPC ............ *A61B 6/502* (2013.01); *A61B 6/0414* (2013.01); *A61B 6/4476* (2013.01)

(58) Field of Classification Search
CPC ......... A61B 6/0414; A61B 6/44; A61B 6/447; A61B 6/4476; A61B 6/4482; A61B 6/502
See application file for complete search history.

(56) References Cited

U.S. PATENT DOCUMENTS 5,664,573 A   9/1997  Shmulewitz
2009/0262887 A1*  10/2009  Iordache .............. A61B 5/6843
378/37

(Continued)

FOREIGN PATENT DOCUMENTS

CN   103876760   6/2014
JP   2012-115335   6/2012

(Continued)

OTHER PUBLICATIONS

International Search Report mailed Jan. 6, 2016 in International Patent Application No. PCT/KR2015/009928.

*Primary Examiner* — Thomas R Artman
(74) *Attorney, Agent, or Firm* — Staas & Halsey LLP

(57) ABSTRACT

There is provided a mammography apparatus capable of delivering a greater load when a breast is released than a load delivered when the breast is compressed by a compression paddle. A mammography apparatus includes a main body having an X-ray generating unit and an X-ray detecting unit, wherein the main body includes a ball screw extending in a vertical direction, a gear unit configured to receive a driving force and be vertically movable along the ball screw, a compression paddle connected to the gear unit and configured to move down in a direction in which the ball screw extends to compress a subject, a handgrip configured to manipulate the compression paddle to be vertically movable, and a power transmission device configured to deliver a driving force delivered from the handgrip to the gear unit, and the power transmission device includes a torque limiter configured to deliver a restricted driving force to the gear unit and a one-way clutch configured to deliver a driving force only when the gear unit moves in one direction.

23 Claims, 8 Drawing Sheets

(56) References Cited

U.S. PATENT DOCUMENTS

| | | | |
|---|---|---|---|
| 2012/0330163 A1* | 12/2012 | Nakabayashi | A61B 5/0095 600/476 |
| 2013/0251113 A1* | 9/2013 | Taku | A61B 5/0091 378/208 |
| 2014/0151179 A1 | 6/2014 | Greuel et al. | |
| 2014/0158489 A1 | 6/2014 | Yang | |
| 2014/0348291 A1* | 11/2014 | Lee | A61B 6/0414 378/37 |
| 2016/0135772 A1* | 5/2016 | Nam | A61B 6/0414 378/37 |
| 2016/0135773 A1* | 5/2016 | Kim | A61B 6/4452 378/37 |

FOREIGN PATENT DOCUMENTS

| | | |
|---|---|---|
| KR | 10-1168308 | 7/2012 |
| KR | 10-2013-0077801 | 7/2013 |
| WO | WO 2013/033100 A1 | 3/2013 |

\* cited by examiner

MAMMOGRAPHY APPARATUS

CROSS-REFERENCE TO RELATED APPLICATIONS

This application claims the benefit of Korean Patent Application No. 10-2014-0158562, filed on Nov. 14, 2014 in the Korean Intellectual Property Office, the disclosure of which is incorporated herein by reference.

BACKGROUND

1. Field

Embodiments of the present disclosure relate to a mammography apparatus capable of delivering variable power.

2. Description of the Related Art

An X-ray imaging apparatus is an apparatus configured to obtain an image of an inside of a subject using X-rays. The X-ray imaging apparatus radiates X-rays to the subject, detects X-rays that pass through the subject, and can image an inside of the subject in a non-invasive manner. Medical X-ray imaging apparatuses may be used to diagnose injuries, diseases and the like inside the subject that cannot be identified externally.

A mammography apparatus among X-ray imaging apparatuses can image a breast of a woman using X-rays. Doctors may view the captured image and diagnose a risk of breast cancer developing.

The mammography apparatus compresses biological tissues inside the breast, radiates X-rays to the breast, and obtains an image. A main body of the mammography apparatus may include a compression paddle capable of compressing the breast and an X-ray detecting unit. The main body may be provided to a stand to be vertically movable.

The compression paddle may move automatically or manually in a vertical direction. In order to restrict a load on a breast compressed by the compression paddle, a power transmission device connected to the compression paddle may include a torque limiter. When the power transmission device includes the torque limiter, a load delivered to the compression paddle may be restricted such that the breast is not compressed at a specific load or more.

SUMMARY

According to an embodiment of the present disclosure, there may be provided a mammography apparatus capable of delivering a greater load when a breast is released than a load delivered when the breast is compressed by a compression paddle.

According to an aspect of the present disclosure, there is provided a mammography apparatus, including a main body having an X-ray generating unit and an X-ray detecting unit, wherein the main body includes a ball screw extending in a vertical direction, a gear unit configured to receive a driving force and be vertically movable along the ball screw, a compression paddle connected to the gear unit and configured to move down in a direction in which the ball screw extends to compress a subject, a handgrip configured to manipulate the compression paddle to be vertically movable, and a power transmission device configured to deliver a driving force delivered from the handgrip to the gear unit, and the power transmission device includes a torque limiter configured to deliver a restricted driving force to the gear unit and a one-way clutch configured to deliver a driving force only when the gear unit moves in one direction.

The one-way clutch may deliver a driving force to the gear unit only when the compression paddle is moved up by the gear unit.

The power transmission device may include a first connecting unit and a second connecting unit, the torque limiter may be provided in the first connecting unit, and the one-way clutch may be provided in the second connecting unit.

When the compression paddle is moved down, a driving force may be delivered to the gear unit through the first connecting unit, and delivery of a driving force through the second connecting unit may be blocked.

When a driving force input by manipulating the handgrip is greater than a permissible level of the torque limiter, only a driving force of a size restricted by the torque limiter may be delivered to the gear unit through the first connecting unit.

When the compression paddle is moved up, a driving force may be delivered to the gear unit through the first connecting unit and the second connecting unit.

The handgrip may be connected to a first shaft, and the torque limiter and the one-way clutch may be provided in a second shaft.

The first shaft and the second shaft may be connected by a belt.

The driving force input through the handgrip may be delivered to the second shaft through the belt.

The one-way clutch may be provided at a side of the second shaft, and the torque limiter may be provided at the other side of the second shaft.

The mammography apparatus may further include a third shaft in which the gear unit is provided.

The mammography apparatus may further include a first belt connecting one side of the second shaft and one side of the third shaft, and a second belt connecting the other side of the second shaft and the other side of the third shaft.

When the compression paddle is moved down, delivery of a driving force through the first belt may be blocked, and a driving force of the second shaft may be delivered to the third shaft through the second belt.

When the compression paddle is moved up, a driving force of the second shaft may be delivered to the third shaft through the first belt and the second belt.

The compression paddle and the power transmission device may be moved up or down integrally.

According to another aspect of the present disclosure, there is provided a mammography apparatus, including: a main body whose both ends are bent to face each other; a compression paddle mounted on the main body to be vertically movable; a lifting unit provided in the main body and configured to move the compression paddle up or down; a power transmission input unit to which a driving force is input; and a first power transmission unit and a second power transmission unit configured to connect the power transmission input unit and the lifting unit, wherein the power transmission unit includes a one-way clutch provided in the first power transmission unit and configured to deliver a driving force through the second power transmission unit only when the compression paddle is moved up; and a torque limiter provided in the second power transmission unit and configured to restrict a size of a driving force delivered through the second power transmission unit.

When the compression paddle is moved down, a driving force may be delivered to the lifting unit through the second power transmission unit.

The lifting unit may include a ball screw provided at the main body and a ball nut engaged with the ball screw.

The power transmission unit and the compression paddle may be connected to the ball nut and move up or down along the ball screw.

The ball nut and the power transmission unit may be connected by a worm gear.

When the compression paddle is moved up, a driving force may be delivered to the lifting unit through the first power transmission unit and the second power transmission unit.

According to another aspect of the present disclosure a power transmission apparatus configured to be installed in a mammography apparatus is disclosed. The power transmission apparatus may include a gear unit configured to connect to a compression paddle and to be disposed at a main body of the mammography apparatus to move the compression paddle up or down, a power transmission input unit to which a driving force is input, a power transmission unit connecting the power transmission input unit and the gear unit, wherein the power transmission unit includes a one-way clutch to selectively deliver the driving force input through the power transmission input unit to the gear unit when the power transmission input unit is operated to move the compression paddle up and to block the driving force input through the power transmission input unit to the gear unit when the power transmission input unit is operated to move the compression paddle down.

According to another aspect of the present disclosure a power transmission apparatus configured to be installed in a mammography apparatus is disclosed. The power transmission apparatus may include a ball screw comprising a ball nut to move up and down in accordance with a rotation of the ball screw, a first shaft comprising first and second handgrips mounted at opposing ends of the first shaft and further comprising a one-way clutch and a torque limiter, a second shaft comprising a worm gear engaged with a worm wheel gear provided at the ball screw and rotationally connected to the first shaft via a belt, and a compression paddle connected to the first shaft and configured to be movable in an up or down direction when the first and second handgrips are rotated.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Hereinafter, a mammography apparatus according to an embodiment of the present disclosure will be described in detail with reference to the drawings.

Figure 1:
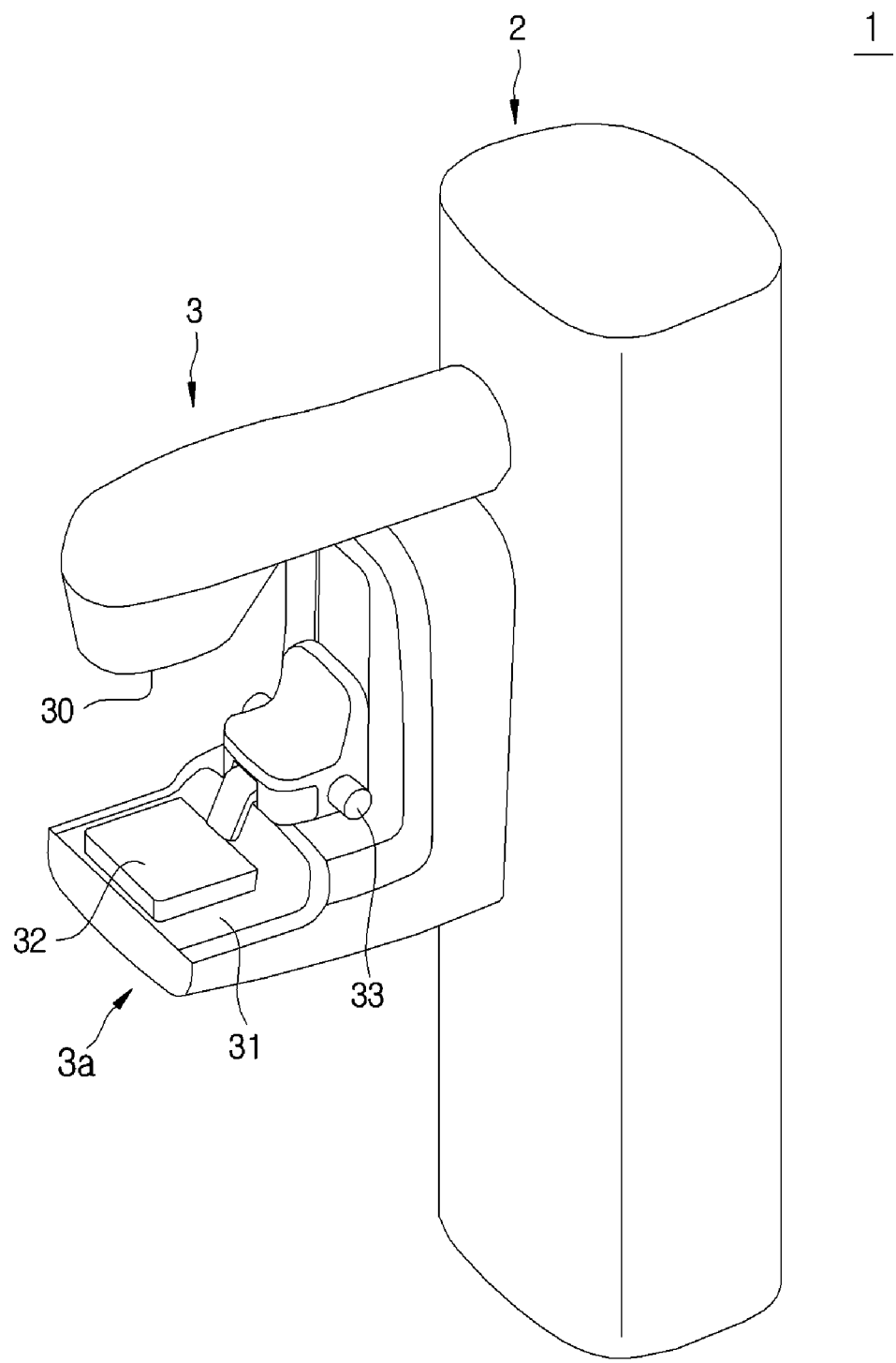
FIG. 1 is a diagram illustrating a mammography apparatus according to an embodiment of the present disclosure.
Figure 2:
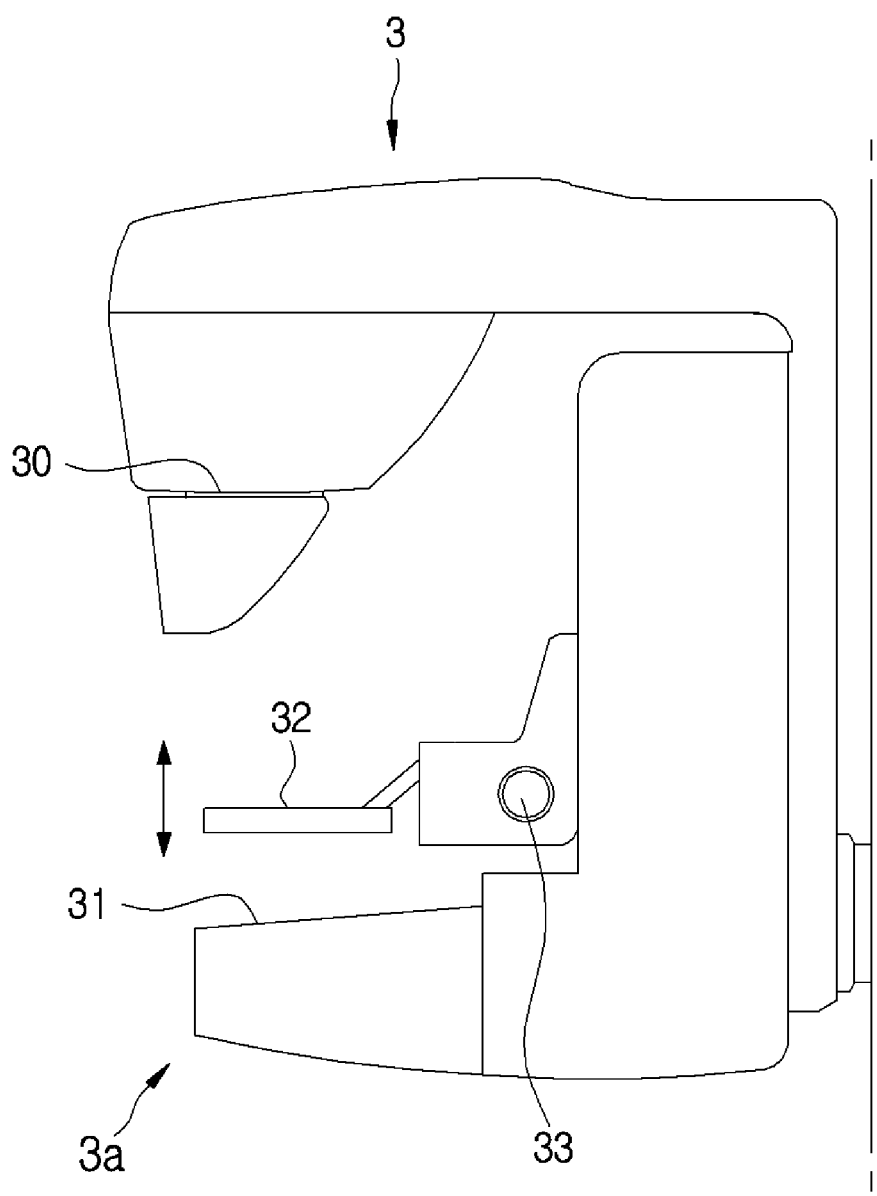
FIG. 2 is a diagram illustrating a part of a main body of a mammography apparatus according to an embodiment of the present disclosure.

FIG. 1 is a diagram illustrating a mammography apparatus according to an embodiment of the present disclosure. FIG. 2 is a diagram illustrating a part of a main body of a mammography apparatus according to an embodiment of the present disclosure.

As illustrated in FIGS. 1 and 2, a mammography apparatus 1 according to the embodiment of the present disclosure includes a stand 2 and a main body 3 connected to the stand 2 to be vertically movable. The main body 3 may perform X-ray imaging on an affected area of a subject.

The mammography apparatus 1 according to the embodiment of the present disclosure is an apparatus configured to obtain an image of an inside of a breast using X-rays. Hereinafter, the breast may be a subject of the mammography apparatus 1.

The main body 3 may include an X-ray generating unit 30 and an X-ray detecting unit 31. The main body 3 has a C-arm shape whose both ends are bent to face each other, and may have one end in which the X-ray generating unit 30 is provided and the other end in which the X-ray detecting unit 31 is provided. The X-ray generating unit 30 and the X-ray detecting unit 31 may face each other. The X-ray generating unit 30 may be positioned in an upper part of the main body 3 and the X-ray detecting unit 31 may be positioned in a lower part of the main body 3.

The X-ray generating unit 30 generates X-rays and radiates the X-rays to the subject. X-rays transmitted through the subject may be detected by the X-ray detecting unit 31. The X-ray detecting unit 31 may convert the detected X-rays into an electrical signal, obtain X-ray data, and transmit the data to a control unit.

When the subject is a breast formed of only soft tissues, compression in a vertical direction is necessary to obtain a more vivid and precise image. Therefore, a compression paddle 32 capable of compressing the subject may be provided. The compression paddle 32 may be positioned between the X-ray generating unit 30 and the X-ray detecting unit 31. The subject may be positioned between the compression paddle 32 and the X-ray detecting unit 31, and the subject may be radiated with X-rays while the subject is compressed by the compression paddle 32.

The compression paddle 32 is vertically movable by a handgrip 33. In order to image the subject, the subject, e.g., the subject's breast, is positioned on the X-ray detecting unit 31, an operator moves the compression paddle 32 down, and thus the compression paddle 32 may compress the subject at an appropriate pressure. When the X-ray generating unit 30 radiates X-rays while the subject is compressed at an appropriate pressure, X-rays transmitted through the subject may be detected by the X-ray detecting unit 31, and X-ray data obtained by the X-ray detecting unit 31 may be transmitted to the control unit. X-ray imaging is performed and then the operator may move the compression paddle 32 up to release a compression state of the subject.

The compression paddle 32 may be manually vertically movable using the handgrip 33, or may be automatically vertically movable using an electrical power transmission device.

In order to ensure safety during X-ray imaging, a force (F) applied by the compression paddle 32 to press the subject may be set to be a predetermined value or less. For example, a force (F) applied by the compression paddle 32 to compress the subject is set to be 300 N (newtons) or less. The power transmission device configured to deliver a driving force to the compression paddle 32 may include a torque limiter 46 (refer to FIG. 5). Due to the torque limiter 46, a force (F) having no more than a predetermined value is delivered to the compression paddle 32.

According to respective weights of the compression paddle 32 and the power transmission device to which the compression paddle 32 is connected, a force necessary for moving the compression paddle 32 up and a force necessary for moving the compression paddle 32 down may have different sizes. Due to the weight of the compression paddle 32 and the weight of the power transmission device, a force of a relatively small size may be used to move the compression paddle 32 down. However, in order to move the compression paddle 32 up, a force necessary for overcoming the weight of the compression paddle 32 and the weight of the power transmission device is further necessary, and thus a force of a relatively greater size needs to be applied.

In this manner, when the compression paddle 32 moves up or down, forces of different sizes need to be applied. However, in the related art, when the compression paddle 32 moves up or down, a size of a force to be delivered is restricted by the torque limiter 46 to a predetermined value or less. Therefore, it is difficult to deliver a force of a different size according to a direction in which the force is delivered.

Hereinafter, a power transmission device configured to deliver variable power such that forces of different sizes may be delivered when the compression paddle 32 is manually moved up or down will be described.

Figure 3:
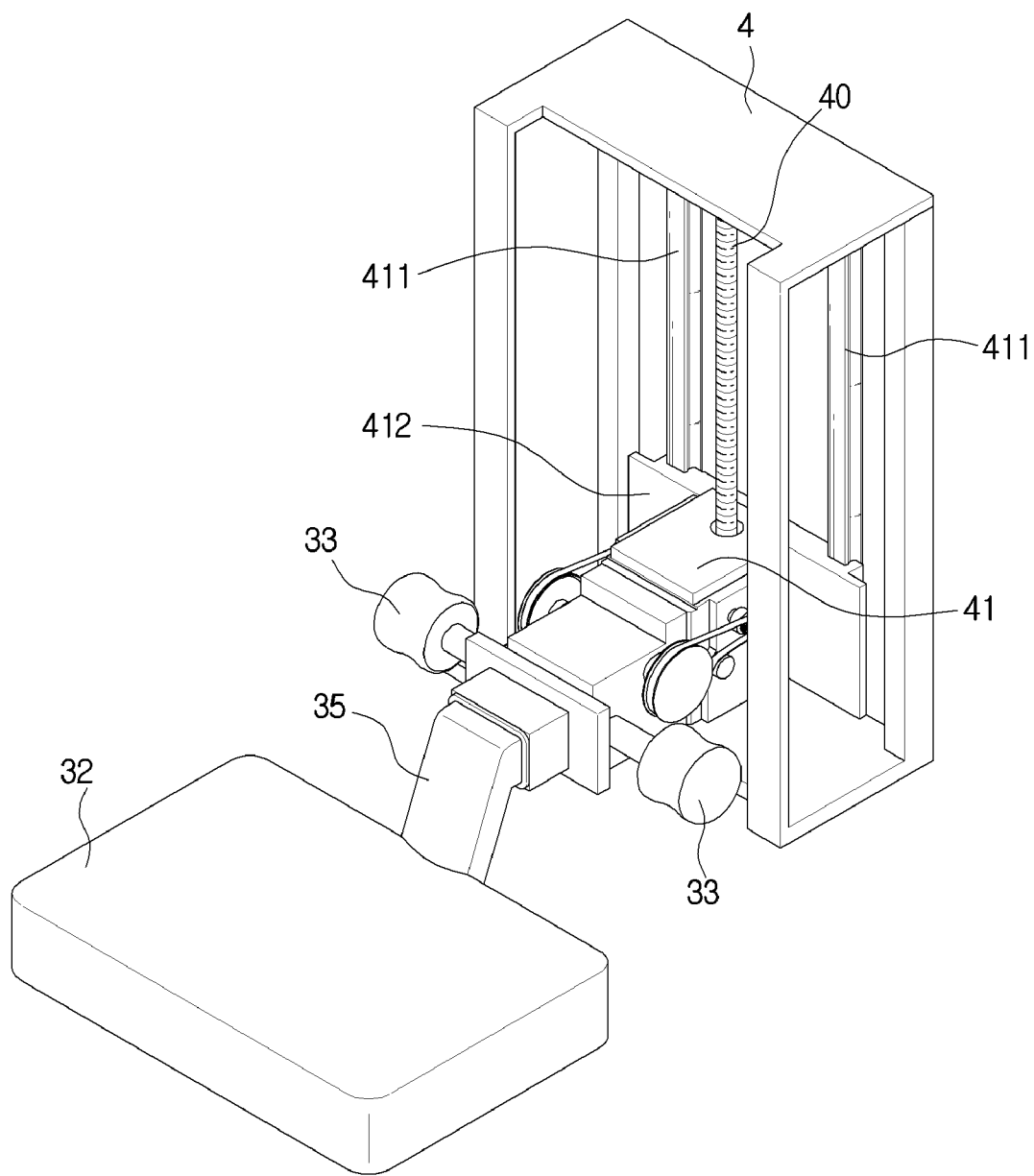
FIG. 3 is a diagram illustrating a part of a configuration of a main body of a mammography apparatus according to an embodiment of the present disclosure.
Figure 4:
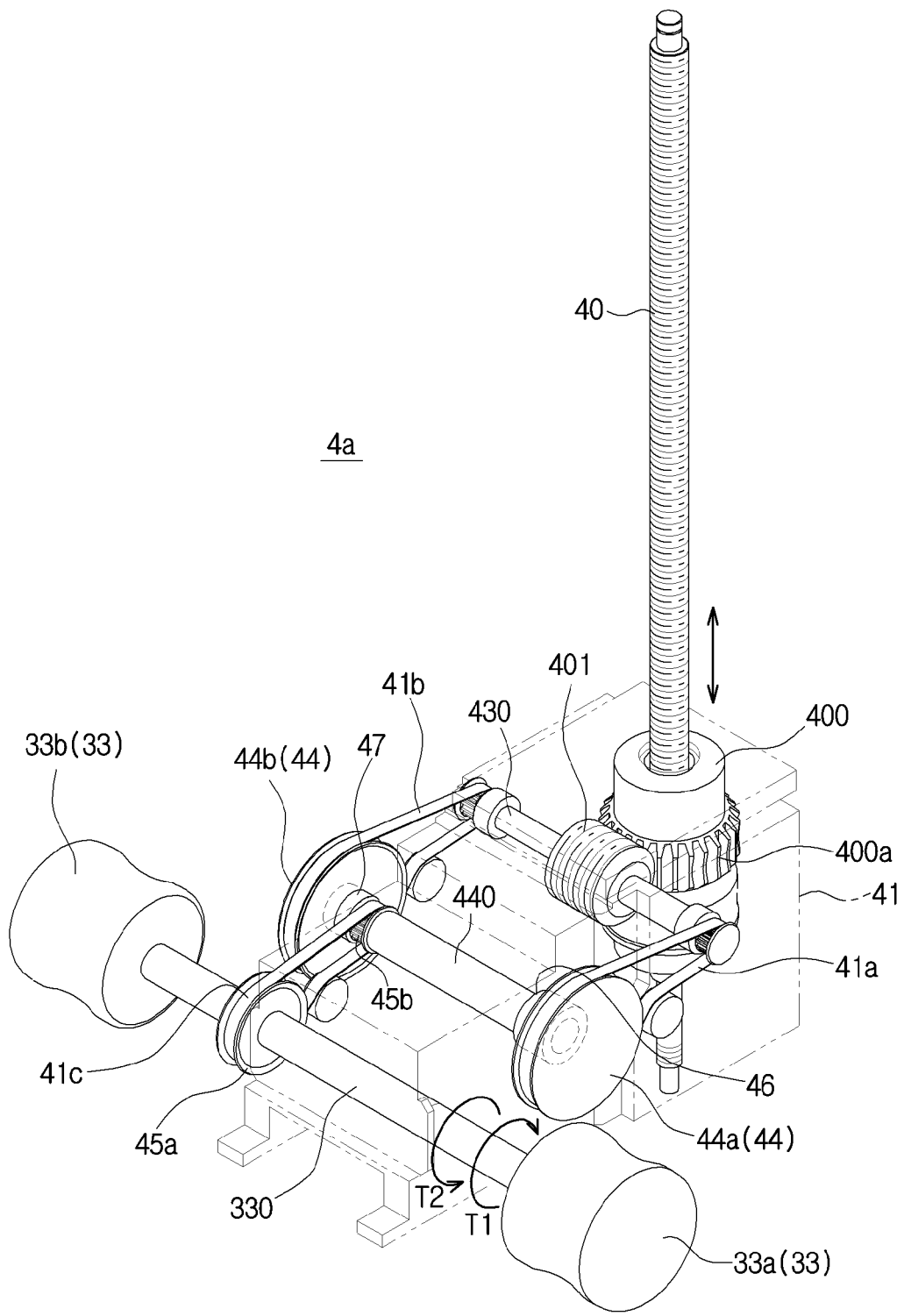
FIG. 4 is a diagram illustrating a state in which a compression paddle according to an embodiment of the present disclosure moves in a vertical direction.

FIG. 3 is a diagram illustrating a part of a configuration of a main body of a mammography apparatus according to an embodiment of the present disclosure. FIG. 4 is a diagram illustrating a state in which a compression paddle according to an embodiment of the present disclosure moves in a vertical direction.

As illustrated in FIGS. 3 and 4, the main body 3 according to the embodiment of the present disclosure may include a power transmission device 4a connected to the compression paddle 32. A ball screw 40 extending in a vertical direction may be provided in the main body 3. The main body 3 may include a frame 4, and the frame 4 may include the ball screw 40. The compression paddle 32 may be connected to the ball screw 40 by the power transmission device. The compression paddle 32 and the power transmission device 4a may move in a vertical direction along the ball screw 40.

The power transmission device 4a may be connected to the ball screw 40 by an assembly of worm gears 400a and 401 and may move in a vertical direction along the ball screw 40. A part of the power transmission device 4a may be accommodated inside a gearbox 41. When a driving force is delivered through the handgrip 33, the power transmission device 4a may move up or down along the ball screw 40 together with the gearbox 41.

A guide 411 configured to guide vertical movement of the gearbox 41 may be provided inside the main body 3. The guide 411 may be separated a predetermined interval from the ball screw 40 and extend in parallel with the ball screw 40. The gearbox 41 may be mounted at a bracket 412 that is vertically slidable along the guide 411. When the gearbox 41 vertically moves along the ball screw 40, the bracket 412 may vertically move along the guide 411, and guide movement of the gearbox 41.

The power transmission device 4a and the compression paddle 32 may be connected by a connecting unit 35. The connecting unit 35 may be connected to a shaft 330 that is connected to the handgrip 33. The compression paddle 32 may move together with the power transmission device 4a.

Figure 5:
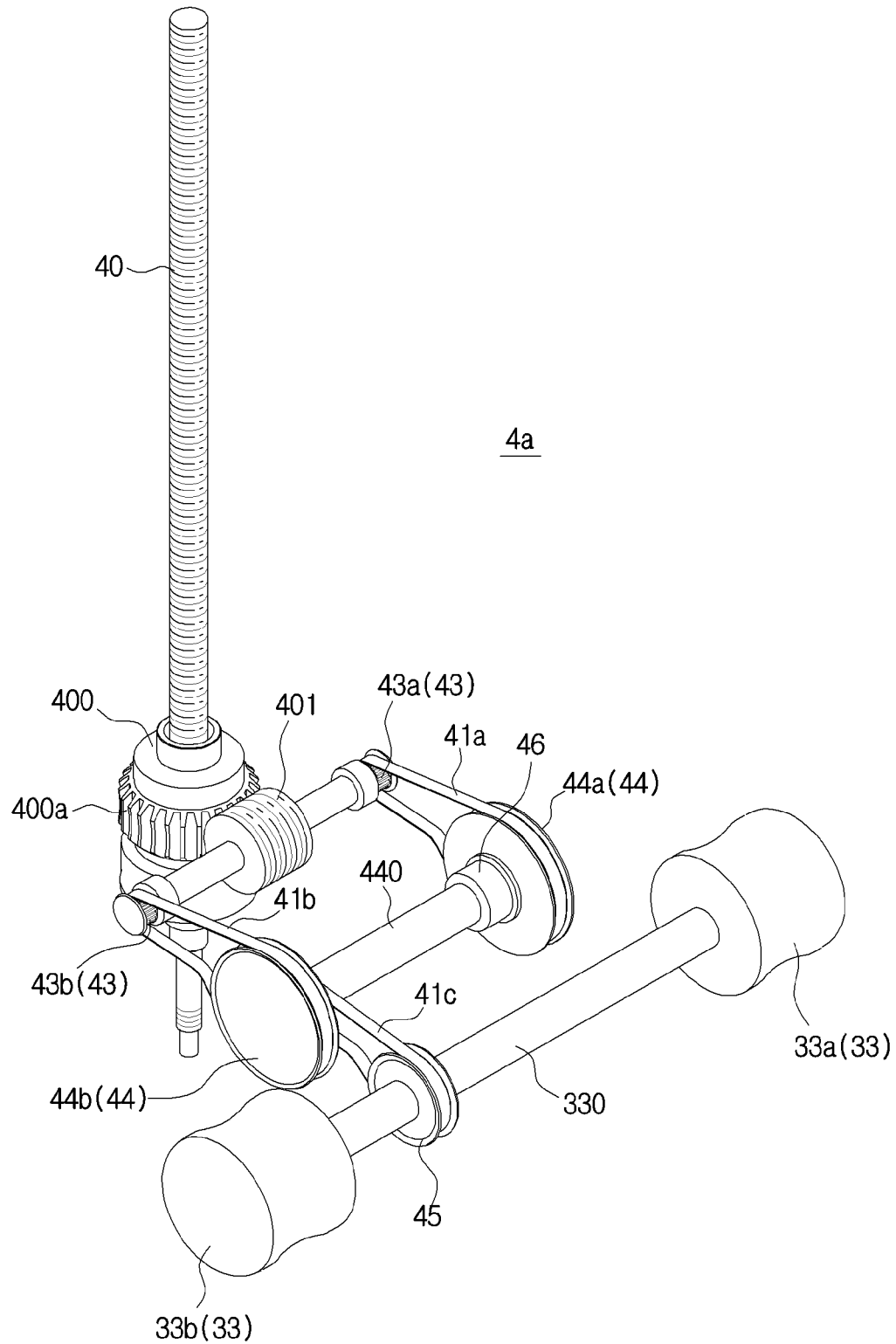
FIG. 5 is a perspective view of a power transmission device for a compression paddle according to an embodiment of the present disclosure.
Figure 6:
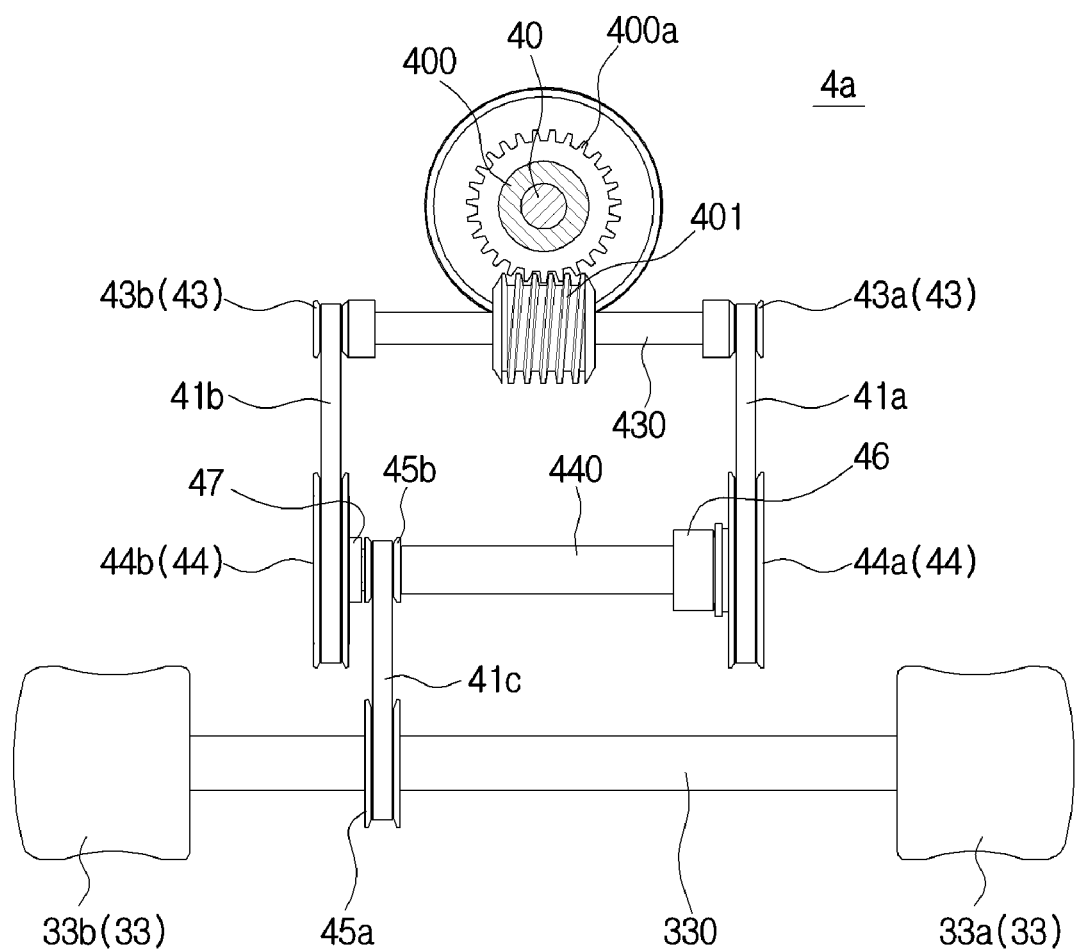
FIG. 6 is a plan view of a power transmission device for a compression paddle according to an embodiment of the present disclosure.

FIG. 5 is a perspective view of a power transmission device for a compression paddle according to an embodiment of the present disclosure. FIG. 6 is a plan view of a power transmission device for a compression paddle according to an embodiment of the present disclosure.

As illustrated in FIGS. 5 and 6, the power transmission device 4a for the compression paddle 32 according to the embodiment of the present disclosure may include a first power transmission unit A, a second power transmission unit B, a third power transmission unit C and a last power transmission unit D. A driving force input to the first power transmission unit A may be delivered to the last power transmission unit D through the second power transmission unit B and the third power transmission unit C.

The first power transmission unit A may include the handgrip 33 that is manually adjustable. The last power transmission unit D may include a ball nut 400 connected to the ball screw 40. The worm wheel gear 400a may be provided at the outer surface of the ball nut 400. The worm wheel gear 400a may be engaged with the worm gear 401. The worm wheel gear 400a and the worm gear 401 may be called the assembly of worm gears 400a and 401.

A driving force input through the handgrip 33 of the first power transmission unit A may be delivered to the assembly of worm gears 400a and 401 through the second power transmission unit B and the third power transmission unit C. Due to the driving force delivered to the assembly of worm gears 400a and 401, the gearbox 41 and the compression paddle 32 connected thereto may vertically move in a direction in which the ball screw 40 extends.

The second power transmission unit B receives a driving force from the first power transmission unit A, and delivers the driving force to the third power transmission unit C. The second power transmission unit B may include the torque limiter 46 and a one-way clutch 47. The driving force input to the second power transmission unit B may be restricted by the torque limiter 46 to a predetermined value or less.

The one-way clutch 47 enables the driving force delivered to the second power transmission unit B to be delivered to the third power transmission unit C in only one direction. Specifically, a driving force, which is input to the first power transmission unit A in order to move the ball nut 400 up along the ball screw 40, passes through the one-way clutch 47 of the second power transmission unit B, and is delivered to the third power transmission unit C. However, a driving force, which is input to the first power transmission unit A in order to move the ball nut 400 down along the ball screw 40, is blocked by the one-way clutch 47, and not delivered to the third power transmission unit C.

In this manner, when the driving force input to the second power transmission unit B is changed and delivered, a driving force necessary for compressing or releasing the subject by the compression paddle 32 may be appropriately delivered.

Hereinafter, detailed configurations of the first power transmission unit A, the second power transmission unit B, the third power transmission unit C and the last power transmission unit D will be described.

The first power transmission unit A includes the handgrip 33 and the first shaft 330 to which the handgrip 33 is connected. Handgrips 33a and 33b may be provided at both sides of the first shaft 330, respectively. A user may grasp the handgrips 33a and 33b to rotate the first shaft 330. As an example, the user may rotate the handgrip 33 in one direction (direction T1) in order to move the compression paddle 32 up, and rotate the handgrip 33 in another direction (direction T2) in order to move the compression paddle 32 down.

The first shaft 330 and a second shaft 440 may be connected by a belt 41c. Pulleys 45a and 45b are provided at the first shaft 330 and the second shaft 440, respectively. The belt 41c may be wound on the pulleys 45a and 45b. A rotational force of the first shaft 330 may be delivered to the second shaft 440 by the belt 41c.

The second shaft 440 and the first shaft 330 may rotate in the same direction. When the first shaft 330 rotates in one direction (direction T1), the second shaft 440 may also rotate in the one direction (direction T1). When the first shaft 330 rotates in another direction (direction T2), the second shaft 440 may also rotate in another direction (direction T2).

The second shaft 440 and a third shaft 430 may be connected by belts 41a and 41b. First pulley 44a and second pulley 44b are provided at each end of the second shaft 440. A third pulley 43a and a fourth pulley 43b, which correspond to the pulleys 44a and 44b provided in the second shaft 440, may be provided in the third shaft 430.

The first belt 41a may be wound on the first pulley 44a provided in the second shaft 440 and the third pulley 43a provided in the third shaft 430. A second belt 41b may be wound on the second pulley 44b provided in the second shaft 440 and the fourth pulley 43b provided in the third shaft 430. A rotational force of the second shaft 440 may be delivered to the third shaft 430 by the first and second belts 41a and 41b.

When the second shaft 440 rotates in one direction (direction T1), the third shaft 430 may rotate in one direction (direction T1). When the second shaft 440 rotates in another direction (direction T2), the third shaft 430 may also rotate in another direction (direction T2). Therefore, when the first shaft 330 rotates in one direction (direction T1), the second shaft 440 and the third shaft 430 may also rotate in one direction (direction T1). When the first shaft 330 rotates in another direction (direction T2), the second shaft 440 and the third shaft 430 may also rotate in another direction (direction T2).

The third shaft 430 may include the worm gear 401. The ball nut 400 that moves up or down in a direction in which the ball screw 40 extends may be provided at the ball screw 40 that vertically extends from a main body 4. The worm wheel gear 400a may be provided at the outer surface of the ball nut 400.

When the third shaft 430 rotates in one direction (direction T1) or another direction (direction T2), the worm gear 401 is engaged with the worm wheel gear 400a and rotates the ball nut 400, and the ball nut 400 may move up or down, respectively, along the ball screw 40 while rotating.

As an example, when the worm gear 401 rotates in one direction (direction T1), the ball nut 400 may move up along the ball screw 40, and when the worm gear 401 rotates in another direction (direction T2), the ball nut 400 may move down along the ball screw 40.

The torque limiter 46 may be mounted at the second shaft 440. In the rotational force delivered from the first shaft 330, a rotational force of a predetermined value or more may not be delivered by the torque limiter 46. For example, when a force of the compression paddle 32 to compress the subject is set to 300 N or less, even if a rotational force, which is greater than a rotational force when a force of the compression paddle 32 to compress the subject is 300 N, is applied to the first shaft 330, the torque limiter 46 provided in the second shaft 440 restricts the rotational force delivered to the second shaft 440 so that only a rotational force at which the compression paddle 32 compresses the subject at a force of 300 N is delivered to the third shaft 430. That is, the rotational force at which a force of the compression paddle 32 to compress the subject is 300 N may be a maximum rotational force of the third shaft 430.

The second shaft 440 may further include the one-way clutch 47. When the torque limiter 46 is provided at a side of the first pulley 44a, the one-way clutch 47 may be provided at a side of the second pulley 44b.

The rotational force of the second shaft 440 may be delivered to the third shaft 430 through the first belt 41a wound on the first pulley 44a and the third pulley 43a when the worm wheel gear 400a is moved up or down. In this case, the rotational force delivered to the third shaft 430 through the first belt 41a may be restricted by the torque limiter 46.

However, the rotational force of the second shaft 440 may be delivered to the third shaft 430 through the second belt 41b wound on the second pulley 44b and the fourth pulley 43b only when the ball nut 400 is caused to be moved up. When the ball nut 400 is caused to be moved down, the rotational force of the second shaft 440 is prevented from being delivered through the second belt 41b by the one-way clutch 47.

When the ball nut 400 moves down, that is, when the compression paddle 32 moves down, the rotational force of the second shaft 440 is delivered through the first belt 41a, and the rotational force delivered to the third shaft 430 through the first belt 41a may be restricted by the torque limiter 46 to a predetermined value or less.

When the ball nut 400 moves up, that is, when the compression paddle 32 moves up, the rotational force of the second shaft 440 may be delivered through the first belt 41a and the second belt 41b. The rotational force delivered through the first belt 41a may be restricted to a predetermined value or less. However, the rotational force delivered through the second belt 41b may be delivered to the third shaft 430 without limitation.

When the compression paddle 32 is moved down, the rotational force of the second shaft 440 may be delivered to the third shaft 430 through only the first belt 41a. The rotational force delivered through the first belt 41a may be restricted by the torque limiter 46 to a predetermined value or less. When the compression paddle 32 moves up, the rotational force of the second shaft 440 may be delivered to the third shaft 430 through the first belt 41a and the second belt 41b. In this case, the rotational force delivered through the first belt 41a is restricted by the torque limiter 46 to a predetermined value or less, but the rotational force delivered through the second belt 41b is not restricted. Therefore, a rotational force greater than a force at which the compression paddle 32 moves down may be delivered to the third shaft 430.

In this manner, when the torque limiter 46 and the one-way clutch 47 are provided in the second shaft 440 at different power transmission shafts, the power transmission device 4a may deliver a force of a different size when the compression paddle 32 is moved down or up. When the compression paddle 32 is moved down, the rotational force may be restricted by the torque limiter 46 to a predetermined value or less and then delivered. When the compression paddle 32 is moved up, a rotational force greater than a force at which the compression paddle 32 is moved down may be delivered through both the power transmission shaft in which the torque limiter 46 is provided and the power transmission shaft in which the one-way clutch 47 is provided. Therefore, weights of the power transmission device 4a and the compression paddle 32 may be overcome and the compression paddle 32 may be easily moved up.

Figure 7:
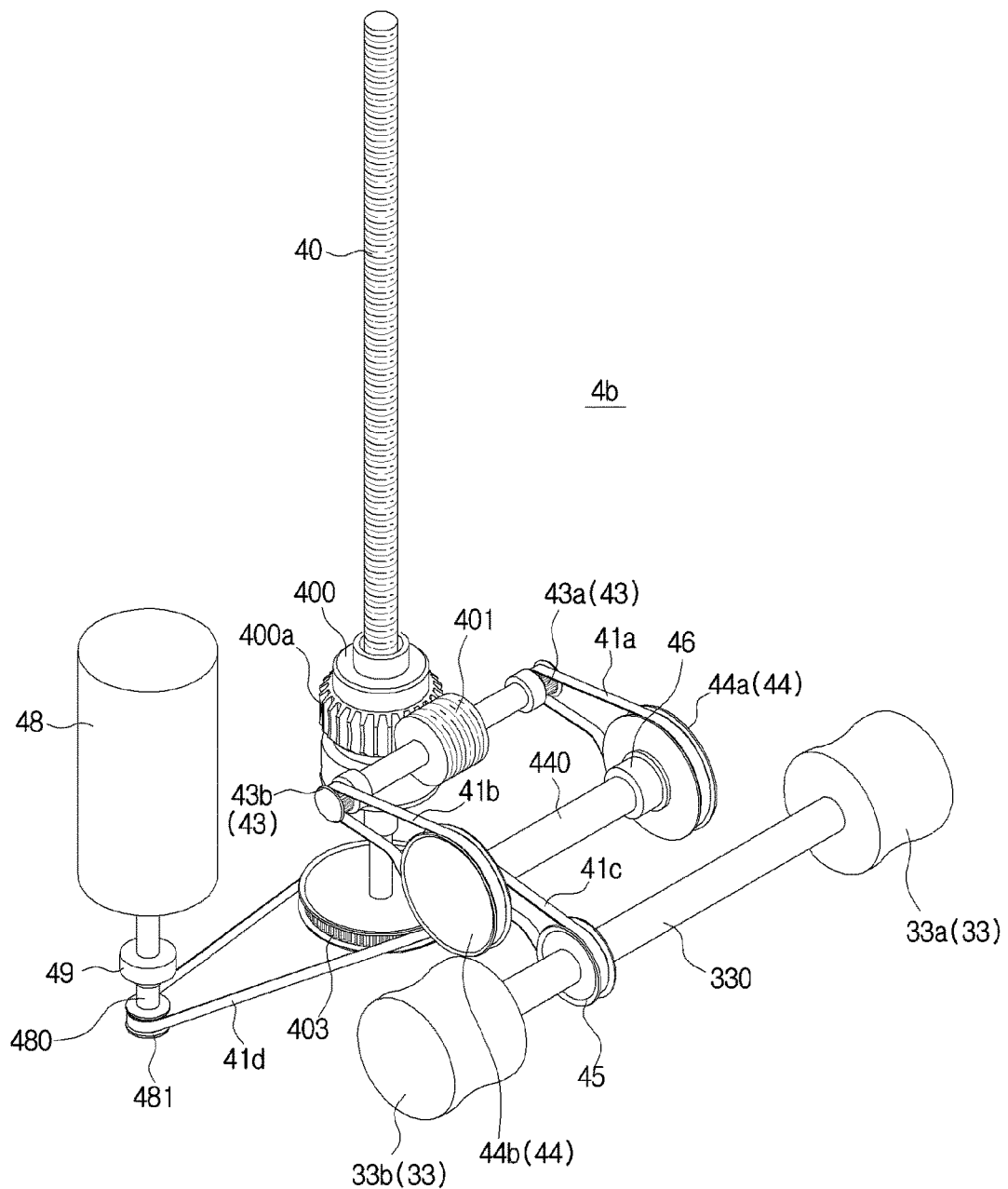
FIG. 7 is a diagram illustrating a power transmission device according to another embodiment of the present disclosure.

FIG. 7 is a diagram illustrating a power transmission device according to another embodiment of the present disclosure.

As illustrated in FIG. 7, the compression paddle 32 (not shown) according to another embodiment of the present disclosure may be automatically or manually moved up or down. A power transmission device 4b according to another embodiment of the present disclosure may further include a motor 48 capable of automatically moving the compression paddle 32 up or down in addition to the power transmission device 4a according to the embodiment of the present disclosure.

The motor 48 may be connected to the ball screw 40 and may rotate the ball screw 40. A torque limiter 49 is provided at a side of the motor 48 and restricts the driving force of the motor 48, and the restricted driving force may be delivered to the ball screw 40.

Pulleys 481 and 403 may be provided at a driving shaft 480 connected to the motor 48 and at a side of the ball screw 40, respectively. A belt 41d may be wound on the pulleys 481 and 403 provided at the driving shaft 480 and the ball screw 40. The driving force of the motor 48 may be delivered to the ball screw 40 through the driving shaft 480 and the belt 41d.

The torque limiter 49 may be provided at a side of the driving shaft 480. Only a driving force of a predetermined value or less may be delivered to the ball screw 40 by the torque limiter 49. The ball screw 40 may receive the driving force of a predetermined value or less due to the torque limiter 49 and rotate in one direction or another direction.

When the ball screw 40 rotates in one direction or another direction, the ball nut 400 provided in the ball screw 40 may be moved up or down. The ball nut 400 may move up or down along the ball screw 40. The worm wheel gear 400a provided at the outer surface of the ball nut 400 and the worm gear 401 provided at a side of the third shaft 430 have a reverse-locking function so that the worm gear 401 prevents rotation of the worm wheel gear 400a due to a load and the compression paddle 32 and the power transmission unit 4a may be stopped. When the ball nut 400 moves up or down along the ball screw 40, the power transmission unit connected to the ball nut 400 and the compression paddle 32 may move up or down.

The motor 48 is connected to the ball screw 40 and may deliver a driving force of a predetermined value or less to the compression paddle 32 by the torque limiter 49. Therefore, when the compression paddle 32 moves up or down, the driving force restricted by the torque limiter 49 may be delivered to the compression paddle 32.

However, since a structure in which the compression paddle 32 may be manually moved up is also provided, the user may rotate the handgrip 33, and move the compression paddle 32 up with a driving force that is greater than a driving force that can be delivered by the motor 48.

Figure 8:
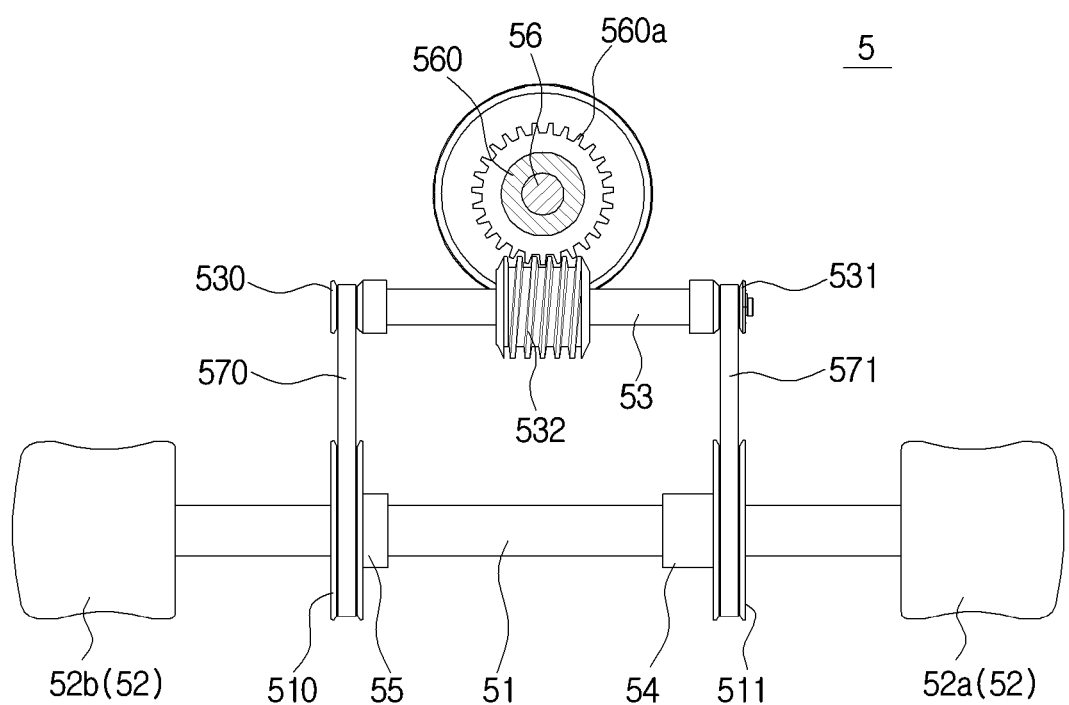
FIG. 8 is a diagram schematically illustrating a power transmission device according to still another embodiment of the present disclosure.

FIG. 8 is a diagram schematically illustrating a power transmission device according to still another embodiment of the present disclosure.

As illustrated in FIG. 8, a power transmission device 5 according to still another embodiment of the present disclosure may have no second power transmission unit B unlike the power transmission unit 4a according to the embodiment of the present disclosure. A first pulley 510 and a second pulley 511 may be provided at a first shaft 51 to which handgrips 52a and 52b are connected. A third pulley 530 and a fourth pulley 531 may be provided at a second shaft 53 separated from the first shaft 51. A first belt 570 may be wound on the first pulley 510 and the third pulley 530. A second belt 571 may be wound on the second pulley 511 and the fourth pulley 531. The compression paddle (not shown) may be connected to the first shaft 51.

A worm gear 532 may be provided at the second shaft 53. The worm gear 532 may be engaged with a worm wheel gear 560a provided at a side of a ball screw 56. A ball nut 560 that may move up or down in a direction in which the ball screw 56 extends may be provided at the ball screw 56. The worm wheel gear 560a may be provided at the outer surface of the ball nut 560. When the second shaft 53 rotates the ball nut 560, at which the worm wheel gear 560a engaged with the worm gear 532 is provided, may rotate and move up or down along the ball screw 56.

The first shaft 51 may include a torque limiter 54. A driving force input through the handgrips 52a and 52b may be restricted by the torque limiter 54 and delivered to the second shaft 53. Therefore, the compression paddle 32 may compress the subject at a force of a predetermined value or less.

The first shaft 51 may further include a one-way clutch 55. The one-way clutch 55 may be provided at a side of the first pulley 510, and the torque limiter 54 may be provided at a side of the second pulley 511. When the compression paddle is moved down, the one-way clutch 55 prevents a driving force from being delivered to the second shaft 53 through the first pulley 510. That is, when a driving force occurs to move the ball nut down along the ball screw by rotating handgrips 52a and 52b, the one-way clutch 55 prevents the first shaft 51 from delivering a driving force to the second shaft 53 via the first pulley 510.

When the handgrips 52a and 52b are rotated in one direction (direction T3), the compression paddle may move down. A driving force input through the handgrips 52a and 52b is delivered to the second shaft 53 through the second belt 571 provided at a side of the second pulley 511. In this case, the driving force of the first shaft 51 may be restricted by the torque limiter 54 provided at a side of the second pulley 511 and delivered to the second shaft 53.

When the handgrips 52a and 52b are rotated in another direction (direction T4), the compression paddle may move up. When the compression paddle moves up, the driving force may be delivered to the second shaft 53 through the first pulley 510. That is, when the compression paddle moves up, the driving force may be delivered to the second shaft 53 through the first belt 570 and the second belt 571. In the driving force delivered through the second belt 571, the driving force restricted by the torque limiter 54 is delivered. However, the driving force is also delivered through the first belt 570 in which the driving force is not limited by the torque limiter 54. Therefore, a driving force greater than a force at which the handgrips 52a and 52b are rotated in one direction (direction T3) may be delivered to the second shaft 53. As a result, the compression paddle may be moved up with a greater force when the compression paddle moves up than when the compression paddle moves down.

In this manner, when the power transmission device capable of moving the compression paddle up or down variably delivers a driving force, it is possible to restrict a maximum value of the force of the compression paddle to compress the subject and the compression paddle can be easily moved up with a greater force.

In a power transmission device according to an embodiment of the present disclosure and a breast imaging apparatus having the same, a load, which is delivered to a compression paddle when the compression paddle compresses or releases a breast, is changed, and thus the breast compressed by the compression paddle can be easily released.

What is claimed is:

1. A mammography apparatus, comprising:
a main body having one end in which an X-ray generating unit is provided and the other end in which an X-ray detecting unit is provided;
a compression paddle positioned between the X-ray generating unit and the X-ray detecting unit and provided at the main body to be vertically movable;
a lifting unit to which the compression paddle is connected to be vertically movable; and
a power transmission device configured to connect the lifting unit and a driving source, and having a one-way clutch configured to deliver a driving force to the lifting unit only when the driving source is operated to move the compression paddle up.

2. The mammography apparatus according to claim 1, wherein the power transmission device includes a torque limiter configured to deliver a restricted driving force to the lifting unit.

3. The mammography apparatus according to claim 2, wherein the power transmission device includes a first connecting unit and a second connecting unit, the torque limiter is provided in the first connecting unit, and the one-way clutch is provided in the second connecting unit.

4. The mammography apparatus according to claim 3, wherein, when the driving source is operated to move the compression paddle up, a driving force is delivered to the lifting unit through the first connecting unit and the second connecting unit.

5. The mammography apparatus according to claim 3, wherein, when the driving source is operated to move the compression paddle down, a driving force is delivered to the lifting unit through the first connecting unit, and delivery of a driving force through the second connecting unit is blocked.

6. The mammography apparatus according to claim 2, wherein the main body includes a handgrip configured to manipulate the compression paddle to be vertically movable, and when a driving force input by manipulating the handgrip is greater than a permissible level of the torque limiter, only a driving force of a size restricted by the torque limiter is delivered to the compression paddle by way of the lifting unit.

7. The mammography apparatus according to claim 6, wherein the handgrip is connected to a first shaft, and the torque limiter and the one-way clutch are provided at a second shaft.

8. The mammography apparatus according to claim 7, wherein the first shaft and the second shaft are connected by a belt.

9. The mammography apparatus according to claim 8, wherein the driving force input through the handgrip is delivered to the second shaft through the belt.

10. The mammography apparatus according to claim 7, wherein the one-way clutch is provided at a side of the second shaft, and the torque limiter is provided at another side of the second shaft.

11. The mammography apparatus according to claim 10, further comprising
a third shaft in which a first gear unit is provided,
wherein the first gear unit is engaged with a second gear unit of a ball screw of the lifting unit that causes the compression paddle to move up or down according to a rotational direction of the first gear unit.

12. The mammography apparatus according to claim 11, further comprising
a first belt connecting one side of the second shaft and one side of the third shaft, and a second belt connecting the other side of the second shaft and the other side of the third shaft.

13. The mammography apparatus according to claim 12, wherein, when the handgrip is operated to move the compression paddle down, delivery of a driving force through the first belt is blocked, and a driving force of the second shaft is delivered to the third shaft through the second belt.

14. The mammography apparatus according to claim 12, wherein, when the handgrip is operated to move the compression paddle up, a driving force of the second shaft is delivered to the third shaft through the first belt and the second belt.

15. The mammography apparatus according to claim 1, wherein the compression paddle and the power transmission device are moved up or down integrally.

16. A mammography apparatus, comprising:
a main body including an X-ray generating unit and an X-ray detecting unit;
a compression paddle positioned between the X-ray generating unit and the X-ray detecting unit;
a lifting unit to which the compression paddle is connected and that is provided at the main body to move the compression paddle up or down;
a power transmission input unit to which a driving force is input; and
a power transmission unit connecting the power transmission input unit and the lifting unit,
wherein the power transmission unit includes a one-way clutch configured to deliver the driving force input through the power transmission input unit to the lifting unit only when the power transmission input unit is operated to move the compression paddle up.

17. The mammography apparatus according to claim 16, wherein the power transmission unit includes a torque limiter, and when the compression paddle is moved down, a size of the driving force delivered to the lifting unit is restricted by the torque limiter.

18. The mammography apparatus according to claim 16, wherein the lifting unit includes a ball screw provided at the main body and a ball nut engaged with the ball screw.

19. The mammography apparatus according to claim 18, wherein the power transmission unit and the compression paddle are connected to the ball nut and move up or down along the ball screw.

20. The mammography apparatus according to claim 18, wherein the ball nut and the power transmission unit are connected by a worm gear.

21. The mammography apparatus according to claim 17, wherein, when the power transmission input unit is operated to move the compression paddle up, a driving force input to the power transmission input unit is delivered to the lifting unit through the power transmission unit without restriction by the one-way clutch.

22. The mammography apparatus according to claim 16, wherein the power transmission input unit includes a handgrip connected to the power transmission unit such that a driving force is manually input.

23. The mammography apparatus according to claim 16, wherein the power transmission input unit includes a motor that is electrically controlled such that a driving force is automatically input.

\* \* \* \* \*